United States Patent [19]

Wellinga et al.

[11] Patent Number: 4,854,961
[45] Date of Patent: Aug. 8, 1989

[54] SUBSTITUTED 2-PHENYLIMINO-OXAZOLIDINE COMPOUNDS HAVING HERBICIDAL ACTIVITY

[75] Inventors: Kobus Wellinga; Jacobus H. H. Eussen, both of Weesp, Netherlands

[73] Assignee: Duphar International Research B.V., Weesp, Netherlands

[21] Appl. No.: 114,863

[22] Filed: Oct. 30, 1987

[30] Foreign Application Priority Data

Nov. 4, 1986 [NL] Netherlands .......................... 8602786

[51] Int. Cl.⁴ .................... A01N 43/00; C07D 263/40
[52] U.S. Cl. ......................................... 71/88; 548/225
[58] Field of Search ............................ 548/225; 71/88

[56] References Cited

U.S. PATENT DOCUMENTS 2,902,356  9/1959  Luckenbaugh ........................ 71/88

OTHER PUBLICATIONS

Aspelund, Chem. Abst., vol. 68 (1968), 39523b.
Aspelund, Chem. Abst., vol. 68 (1968), 59467q.
Brooker et al, Chem. Abst., vol. 78 (1973), 148982c.

Primary Examiner—Anton H. Sutto
Assistant Examiner—Cecilia Shen

Attorney, Agent, or Firm—Stevens, Davis, Miller & Mosher

[57] ABSTRACT

The invention relates to a herbicidally and/or algicidally active compound of the general formula

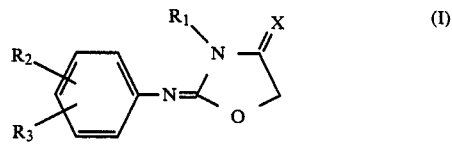

wherein
 $R_1$ is a substituted or non-substituted alkyl group having 1–6 carbon atoms, or an alkenyl or alkynyl group having 2–6 carbon atoms;
 $R_2$ is a halogen atom; a nitro group; a cyano group; a substituted or non-substituted benzyl, phenyl, phenoxy, phenylthio, phenylsulphinyl, phenylsulphonyl or phenylsulphonyloxy group; or a halogenated or non-halogenated alkyl, alkoxy, alkylthio, alkylsulphinyl, alkylsulphonyl or alkylsulphonyloxy group having 1–4 carbon atoms;
 $R_3$ is a hydrogen atom, a halogen atom, or an alkyl group having 1–4 carbon atoms; and
 X is O or S;

or a salt of this compound with an organic or inorganic acid.

7 Claims, No Drawings

SUBSTITUTED 2-PHENYLIMINO-OXAZOLIDINE COMPOUNDS HAVING HERBICIDAL ACTIVITY

The invention relates to new substituted 2-phenylimino-oxazolidine compounds and to a method of preparing the new compounds. The invention also relates to herbicidal and/or algicidal compositions based on the new compounds, and to the use of the said compositions to prevent and/or control undesired plant growth.

Plants which in a given situation are considered to be undesired may be termed weeds. Weed control may generally be carried out after or before emergence of the weeds; agents which have for their object to control the weeds after the emergence thereof are termed post-emergence herbicides, the other ones pre-emergence herbicides. So for controlling or preventing weeds, the weeds themselves or the plot in which they occur may be treated. In agriculture, horticulture and forestry both types of herbicides are used, if so necessary, to ensure an uninhibited growth of the crop during the whole growth period. However, one single application is to be preferred which, when a pre-emergence herbicide is used, is usually carried out prior to, simultaneously with, or immediately after sowing or planting the crop, and, when a post-emergence herbicide is used, before the emerged weeds start hindering the growth of the crop. Pre-emergence herbicides are usually applied before the crop is standing so that damage to the crop is avoided when the herbicide is used. Moreover, sowing of the crop and providing the herbicide in the soil destined for the crop can be carried out in one operation. On the other hand, post-emergence herbicides can often be used more efficiently. The use of pre-emergence herbicides may still be distinguished in pre-emergence application in a narrower sense, i.e. application of the herbicide by a surface treatment of the plot in question, and so-called p.s.i.-application (37 pre-sowing soil incorporated"). In the latter application the herbicide is usually mixed through the top layer of the soil prior to sowing or planting the crop.

It stands to reason that in addition to the activity also the selectivity of the herbicide used is of great importance. In fact, the undesired plants must be controlled or the growth of the undesired plants must be suppressed, but the growth of the crop may not be detrimentally influenced by the herbicide used. An ideal herbicide must control the weeds in the crop during the whole growth season of the crop after a single application in a low dosage. The herbicide must be capable of not only controlling all types of weeds, but also of killing both the seedlings and the growing plants of these weeds, as well as preventing the germination of the weed seeds. However, the herbicide may not exert any detrimental influence on the crops on which it has been provided. It will be obvious that none of the herbicides presently in use can satisfy these conditions simultaneously and hence is ideal. Effective weed control is usually associated with noticeable damage to the crop, while a herbicide which in a given dosage does not have any detrimental influence on the crop usually does not effectively control all the weeds in the same dosage. It will be clear from the above that small differences in herbicidal activity and in influence on the crop may already be of great importance in the evaluation of herbicides for their practical applicability.

Undesired growth of algae is an ever increasing phenomenon in surface waters, such as irrigation canals and drainage canals, fish-ponds, wet rice-fields, and the like. The quality of the flow of the water can be very detrimentally influenced by said growth of algae, as well as, as in the last example, the growth of the crop. Algae can also adhere to walls which are in contact with water, for example ship's hulls and wooden campshots. As a result of this a more frequent maintenance of the walls becomes necessary; in addition the algae limit the speed of the ship. Consequently an agent to prevent or to control algae is of great importance. When applied to surface water, such an agent, however, should satisfy very stringent environmental requirements because only the growth of algae in the water is to be controlled, but the evolution of other organisms living in the water may not be detrimentally influenced. Therefore the choice of a suitable algicide is very critical. Aquatic weeds may cause comparable problems as algae in surface waters, such as irrigation and drainage canals: see above.

Substituted 2-phenylimino-oxazolidine compounds for herbicidal application are disclosed in U.S. Pat. No. 2,902,356, for example, 2-(4-chlorophenylimino)-3-methyloxazolidine. As will become apparent from the examples, this compound, however, does not show any herbicidal activity in a dosage conventionally used for herbicidal application.

It is the object of the invention to provide compounds having a herbicidal activity and selectivity suitable for practical application and/or a suitable algicidal activity. According to the present invention this object can be achieved by means of a compound of the general formula

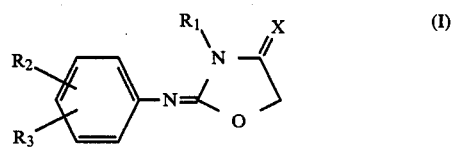

(I)

wherein
$R_1$ is a substituted or non-substituted alkyl group having 1-6 carbon atoms, or an alkenyl or alkynyl group having 2-6 carbon atoms;
$R_2$ is a halogen atom; a nitro group; a cyano group; a substituted or non-substituted benzyl, phenyl, phenoxy, phenylthio, phenylsulphinyl, phenylsulphonyl or phenylsulphonyloxy group; or a halogenated or non-halogenated alkyl, alkoxy, alkylthio, alkylsulphinyl, alkylsulphonyl or alkylsulphonyloxy group having 1-4 carbon atoms;
$R_3$ is a hydrogen atom, a halogen atom, or an alkyl group having 1-4 carbon atoms; and
X is O or S;
or a salt of this compound with an organic or inorganic acid.

If $R_1$ is a substituted alkyl group, the substituent may be chosen from various atoms and groups, for example, halogen and hydroxy. If $R_2$ is a substituted phenyl or benzyl group, these groups may be substituted by various substituents, preferably halogen, lower alkyl, lower alkoxy, lower haloalkyl, lower haloalkoxy, nitron, cyano and/or lower alkoxycarbonyl.

As particularly suitable is to be considered a compound of the general formula

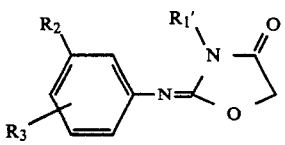 (II)

wherein

R₂ is a substituent having the meaning given hereinbefore and which is attached to the benzene ring in the meta position with respect to the imino-N, R₃ also has the meaning given hereinbefore, and R₁' is an alkyl group having 1–4 carbon atoms, or a salt of the said compound with an organic or inorganic acid.

A compound of the general formula

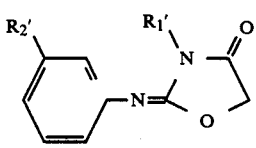 (III)

wherein

R₁' has the meaning given hereinbefore, and

R₂' is a halogenated alkyl, alkoxy, alkylsulphinyl, alkylsulphonyl or alkylthio group having 1–4 carbon atoms, or a salt of the said compound with an organic or inorganic acid, has proven to be pre-eminently active and is hence particularly suitable for use in a herbicidal and/or algicidal composition.

Examples of new 2-phenylimino-oxazolidine compounds according to the invention which may be used in herbicidal compositions are:

(1) 2-(3-trifluoromethylphenylimino)-3-methyloxazolidinone-4.

(2) 2-(3-trifluoromethylphenylimino)-3-ethyloxazolidinone-4.

(3) 2-(3-chlorophenylimino)-3-methyloxazolidinone-4, (4) 2-(3-chloro-4-fluorophenylimino)-3-methyloxazolidinone-4, (5) 2-(3-trifluoromethylthiophenylimino)-3-allyloxazolidinone-4, (6) 2-(3-trifluoromethoxyphenylimino)-3-methyloxazolidinone-4, (7) 2-(3-nitrophenylimino)-3-methyloxazolidinone-4, (8) 2-[3-(1,1,2,3,3,3,-hexafluoropropoxy)phenylimino]-3-methyloxazolidinone-4, (9) 2-[3-(2-chloro-1,1,2-trifluoroethoxy)phenylimino]-3-methyloxazolidinone-4,

(10) 2-[3-(1,1,2,2-tetrafluoroethoxy)phenylimino]-3-methyloxazolidinone-4,

(11) 2-(3,5-dimethylphenylimino)-3-methyloxazolidinone-4,

(12) 2-(3-methylphenylimino)-3-methyloxazolidinone-4,

(13) 2-(3-methoxyphenylimino)-3-methyloxazolidinone-4,

(14) 2-(3-cyanophenylimino)-3-methyloxazolidinone-4,

(15) 2-(3-trifluoromethyl-4-chlorophenylimino)-3-methyloxazolidinone-4,

(16) 2-(3-ethylphenylimino)-3-methyloxazolidinone-4,

(17) 2-(3-methylthiophenylimino)-3-methyloxazolidinone-4,

(18) 2-(3-trifluoromethylthiophenylimino)-3-methyloxazolidinone-4,

(19) 2-(3-benzylphenylimino)-3-methyloxazolidinone-4,

(20) 2-(3-bromophenylimino)-3-methyloxazolidinone-4,

(21) 2-(3-bromophenylimino)-3-ethyloxazolidinone-4,

(22) 2-(3-phenylphenylimino)-3-methyloxazolidinone-4,

(23) 2-(4-chlorophenylimino)-3-methyloxazolidinone-4,

(24) 2-(4-fluorophenylimino)-3-methyloxazolidinone-4,

(25) 2-(4-trifluoromethylphenylimino)-3 methyloxazolidinone-4,

(26) 2-(3-difluoromethylphenylimino)-3-methyloxazolidinone-4,

(27) 2-(4-nitrophenylimino)-3-methyloxazolidinone-4,

(28) 2-(3-methylsulphonyloxyphenylimino)-3-methyloxazolidinone 4,

(29) 2-(4-bromophenylimino)-3-methyloxazolidinone-4,

(30) 2-(3-trifluoromethylsulphinylphenylimino)-3-methyloxazolidinone-4,

(31) 2-(3-trifluoromethylsulphonylphenylimino)-3-methyloxazolidinone-4,

(32) 2-(3-difluoromethoxyphenylimino)-3-methyloxazolidinone-4,

(33) 2-(3-phenylsulphonylphenylimino)-3-methyloxazolidinone-4,

(34) 2-(3-nitro-4-fluorophenylimino)-3-methyloxazolidinone-4,

(35) 2-(3-trifluoromethylphenylimino)-3-methyloxazolidine-4-thione,

(36) 2-[3-(1,1,2,2-tetrafluoroethylthio)phenylimino]-3-methyloxazolidinone-4,

(37) 2-[3-(1,1,2,3,3,3-hexafluoropropylthio)-phenylimino]-3-methyloxazolidinone-4,

(38) 2-[3-(1,1,2,2-tetrafluoroethylsulphonyl)-phenylimino]-3-methyloxazolidinone-4,

(39) 2-(3-isopropoxyphenylimino)-3-methyloxazolidinone-4,

(40) 2-(3-difluoromethylsulphonylphenylimino)-3-methyloxazolidinone-4,

(41) 2-(3-ethylthiophenylimino)-3-methyloxazolidinone-4,

(42) 2-(3-n-propylthiophenylimino)-3-methyloxazolidinone-4,

(43) 2-(3-trifluoromethylsulphonyloxyphenylimino)-3-methyloxazolidinone-4,

(44) 2-(3-n-propylsulphonylphenylimino)-3-methyloxazolidinone-4,

(45) 2-(3-difluoromethylthiophenylimino)-3-methyloxazolidinone-4,

(46) 2-[3-(1,1,2,3,3,3-hexafluoropropylsulphonyl)-phenylimino]-3-methyloxazolidinone 4, and

(47) 2-[3-(2,2,2-trifluoroethoxy)phenylimino]-3-methyloxazolidinone-4.

The substances according to the invention may be used for the control of undesired plant growth. The term "plants" should be interpreted broadly and also includes aquatic plants and algae. Although the new compounds have an interesting post-emergence herbicidal activity, their activity as pre-emergence herbicides still is most striking. Therefore the compounds according to the invention are preferably used as pre-emergence (including p.s.i.) herbicides for the control of monocot weeds, for example, *Poa annua* (annual bluegrass), *Avena fatua* (wild oats), *Alopecurus myosuroides* (blackgrass), *Panicum miliaceum* (millet) and *Echinochloa crusgalli* (barnyard grass), and of dicot weeds, for example, *Galinsoga parviflora* (small-flowered g.), *Galium aparine* (cleavers), *Chenopodium album* (common lambsquarters), *Datura stramonium* (jimsonweed),

*Polygonum convolvulus* (wild buckwheat), *Capsella bursa-pastoris* (shepherd's purse), *Stellaria media* (chickweed), *Senecio vulgaris* (common groundsel), *Veronica arvensis* (common speedwell), *Ipomoea purpurea* (common morning glory's), *Matricaria spp.* (mayweeds), *Amaranthus spp.* (pigweeds), *Solanum nigrum* (black nightshade), *Spergula spp.* (spurrey), *Urtica dioca* (stinging nettle), *Polygonum aviculare* (knotgrass), *Sonchus arvensis* (field sow thistle), *Silybum marianum*, (milk thistle), *Xanthium pensylvanicum, Ipomoea muricata, Ipomoea hederacea, Ipomoea lucunosa, Cassia obtusifolia, Sida spinosa, Anoda cristate, Abutilon theoohrasti, Portulaca oleracea*, etc. in various crops, for example, in cereals e.g. wheat, rice, oats and barley, in leguminosae, e.g. bean, pea, soya, peanut and lucerne, in maize, in sunfower, in cotton, in beets and in pasture. Further the substances according to the invention may be used for the control of aquatic weeds and/or various kinds of algae, such as *Vaucheria, Cladophora, Mougeotia, Hydrodiction, Spirogyra, Eudogonium sp.* and *Enteromorpha*.

For practical application, the substances in accordance with the invention are processed to compositions. In such compositions the active substance is mixed with solid carrier material or dissolved or dispersed in liquid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersing powders, miscible oils, granules and pellets.

Dispersible powders, pastes and miscible oils are compositions in concentrate form which are diluted prior to or during use.

The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/-suspension, if desired in the presence of a binder, on granular carrier material, for example porous granules (for example pumice and attaclay), mineral non-porous granules (sand or ground marl), organic granules (for example, dried coffee grounds, cut tobacco stems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers and then glomulating the mixture to the desired particle size.

Dusting powders can be obtained by intimately mixing the active substance with an inert solid powdered carrier material, for example, talcum.

Dispersible powders are prepared by mixing 10 to 80 parts by weigt of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally other additives, if desired.

For the preparation of miscible oils the active compound is dissolved in a suitable solvent which preferably is poorly water-miscible, and one or more emulsifiers are added to this solution. Suitable solvents are, for example, higher alcohols, e.g. lauryl alcohol, decanol and octanol, further xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily water-miscible liquid, for example, a glycol, a glycol ether or dimethyl formamide, to which solution a dispersing agent and, if desired, a surface-active substance has been added. When diluting with water shortly before or during spraying, an aqueous dispersion of the active substance is then obtained.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the composition to the plant. Furthermore, a substance may be added to reduce the phytotoxicity of the active substance, carrier material or auxiliary substance, for example, wool fat or wool fatty alcohol.

Plant growth regulating and/or pesticidal compounds known per se may also be incorporated in the compositions according to the invention. As a result of this the activity spectrum of the composition is widened and synergism may occur. In addition fertilizers may be added to the composition.

The following known plant growth regulating and-/or herbicidal compounds and fungicidal compounds are to be considered for use in combination compositions, in addition to insecticidal and acaricidal compounds known per se.

Herbicides, for example:
1. phenoxy compounds, for example, (2,4-dichlorophenoxy)acetic acid, 4-chloro-o-tolyloxyacetic acid, and 2-[4-(5-trifluoromethyl-2-pyridyloxy)phenoxy]-propionic acid butyl ester;
2. carboxylic acids, for example, 3-amino-2,5-dichlorobenzoic acid, 3,6-dichloro-2-methoxybenzoic acid and salts thereof, and N-1-naphthylphthaliminic acid and salts thereof;
3. nitro compounds and amides, for example, 2,6-dinitro-N,N-dipropyl-4-trifluoromethylaniline, N-(2-chloroethyl)-2,6-dinitro-N-propyl-4-trifluoromethylaniline, N-(1-ethylpropyl)-3,4-dimethyl-2,6-dinitroaniline, N-(3,4-dichlorophenyl)propionamide, 2-chloro-2',6'-diethyl-N-(methoxymethyl)acetanilide, and 2-chloro N-(2,6-dimethylphenyl)-N-(1-H-pyrazol-1-ylmethyl)acetamide;
4. carbamates, for example, 1-isopropyl-3-chlorophenyl carbamate, S-ethyl diisobutylthiocarbamate, 1-(ethylcarbamoyl)ethylphenylcarbamate, 2,3-dichloroallyl diisopropylthiocarbamate, 2,3,3-trichloroallyl diisopropylthiocarbamate, methyl sulphanilylcarbamate, and S-(p-chlorobenzyl)diethylthiocarbamate;
5. heterocyclic nitrogen compounds, for example 3-amino-1H-1,2,4-triazole, 3,5,6-trichloro-2-pyridyloxyacetic acid, 4-amino-3,5,6-trichloropyridine-2-carboxylic acid, 1,2-dimethyl-3,5-diphenyl- 1H-pyrazolium methyl sulphate, 5-amino-4-chloro-2-phenyl-3(2H)-pyridazinone, 4-chloro-5-(methylamino)-2[3-(trifluoromethyl)phenyl]-3(2H) -pyridazinone, 4,5-dimethoxy-2-phenyl-3-(2H)-pyridazinone, 3-chloro-4-chloromethyl-1-(3-trifluoromethylphenyl)-2-pyrrolidone, 1-methyl-3-phenyl-5-[3-(trifluoromethyl)phenyl]-4-(1H)-pyridinone, sym. triazines (for example, 2-chloro-4-ethylamino-6-isopropylamino-1,3,5-triazine and 2-chloro-4-(1-cyano-1-methylethylamino)-6-ethylamino-1,3,5-trizine), sulphonyl urea compounds, (for example, 1-(2-chlorophenylsulphonyl)-3-(4-methoxy-6-methyl-1,3,5-triazin-2-yl)urea and 2-[3-(4,6-dimethylpyrimidin-2-yl)ureidosulphonyl]benzoic acid), and imidazolidones (for example, 2-(3-carboxyquinolyl)-5-isopropyl-5-methylimidazolidone-4);
6. urea compounds, for example, 3-(3,4-dichlorophenyl)-1,1-dimethylurea, 3-[4-(4-chlorophenoxy)-phenyl]-1,1-dimethylurea, 1,1-dimethyl-3-[3-(trifluoromethyl)phenyl]-urea, 3-(3-chloro-4-methylphenyl)-1,1-dimethylurea, 5-bromo-3-sec. -butyl- 6-methyluracil, 1-benzothiazol-2-yl-1,3-dimethylurea, 3-(4-isopropylphenyl)-1,1-dimethylurea, and 3-(3-chloro-4-methoxyphenyl)-1,1-dimethylurea;
7. nitrophenyl ethers, for example, 2,4-dichlorophenyl 3-methoxy-4-nitrophenyl ether, 5-[2-chloro-4-(trifluoromethyl)phenoxy]- 2-nitrobenzoic acid, 2-chloro-4-trifluoromethylphenyl 3-ethoxy-4-nitrophenyl ether, methyl 4-(2,4-dichlorophenoxy)-2-nitrobenzoate, ethyl 2-[{2 nitro-5-(2-chloro-4-trifluoromethylphenoxy)}phenylcabonyloxy]propionate and 2-chloro-4-trifluoromethylphenyl 3-methylsulphonylcarbamoyl-4-nitrophenyl ether;
8. nitriles, for example, 2,6-dichlorobenzonitrile, 3,5-dibromo-4-hydroxybenzonitrile and 4-hydroxy-3,5-diiodobenzonitrile;
and further: ethyl 2(N-benzoyl-3,4-dichloroanilino)propionate, methyl N-benzoyl-N-(3-chloro-4-fluorophenyl)-2-aminopropionate, butyl 2-[4-(5-trifluoromethyl-2-pyridyloxy)phenoxy propionate, 2-(3,5-dichlorophenyl)-2-(2,2,2-trichloroethyl)oxirane, S-ethyl N,N-hexamethylene thiocarbamate, 5-tert.butyl-3-(2,4-dichloro-5-isopropoxyphenyl)-1,3,4-oxadiazol-2(3H) one, N-(phosphonomethyl)glycine or salts thereof, methyl 2-[4-(2,4-dichlorophenoxy)phenoxy]propionate, 3-isopropyl-(1H)-2,1,3-benzothiadiazin-4(3H)-one, 2,2-dioxide and 2-(1 ethoxyiminobutyl)-5-[2-(ethylthio)-propyl]-3-hydroxycyclohex-2-enone.

Plant growth regulators, for example:
gibberellic acid, α-cyclopropyl-α-(4-methoxyphenyl)-5-pyrimidine methanol, 2-chloroethyltrimethylammonium salts, 2,3:4,6-di-O-isopropylidene-α-L-xylo-2-hexulofuranosonic acid sodium, 2-chloroethyl phosphonic acid, N,N-bis(phosphonomethyl)glycine, 1,1-dimethylpiperidinium chloride)N-[2,4-dimethyl-5-(trifluoromethylsulphonylamino)phenyl]acetamide, maleic acid hydrazide, 2-(1-naphthyl) acetic acid, and fatty acids or lower esters thereof.

Fungicides, for example:
1. organic tin compounds, for example, triphenyltin hydroxide and triphenyltin acetate;
2. alkylene bisdithiocarbamates, for example, zinc ethylene bisdithiocarbamate and manganese ethylenebisdithiocarbamate;
3. 1-acyl or 1-carbamoyl-N-benzimidazole(-2) carbamates and 1,2-bis(3 alkoxycarbonyl-2-thiureido)benzene and furthermore, 2,4-dinitro-6-(1-methylheptylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidin-4-yl-dimethylsulphamate, 1-(4-chlorophenoxy)-3,3-dimethyl-1(1,2,4-triazol 1-yl)-2-butanone, 1-[2-(2,4-dichlorophenyl)-4-propyl-1,3-dioxolan-2-ylmethyl]]-1H-1,2,4-triazole, 2,4'-difluoro-α-(1H-1,2,4-triazol-1-ylmethyl)benzhydryl alcohol, α-(2-chlorophenyl)-α-(4-fluorophenyl)-5-pyrimidinemethanol, α-(2-chlorophenyl)-α-(4-chlorophenyl)-5-pyrimidinemethanol, 1-(isopropylcarbamoyl)-3-(3,5-dichlorophenyl)-hydantoin, N-(1,1,2,2-tetrachloroethylthio)-4-cyclohexene-1,2-carboximide, N-trichloromethylthio-4-cyclohexene-1,2-dicarboximide, N-tridecyl-2,6-dimethylmorpholine, 5,6-dihydro-2-methyl 1,4-oxathiine-3-carboxanilide, metal salts of ethyl phosphite, and N-(2,6-dimethylphenyl)-N-(methoxyacetyl)alanine methyl ester, or mixtures of these compounds.

The dosages of the composition according to the invention desired for practical application will, of course, depend on various factors, for example, field of application, selected active substance, form of composition, nature and size of the weeds or algae and the crops, and the weather conditions.

In general it holds that favourable results can be achieved with a dosage which corresponds to 0.01 to 10 kg of the active substance per hectare, preferable 0.1 to 3 kg per hectare.

It has been found that the herbicidal activity of the compositions according to the invention may increase considerably by the use of suitable adjuvants, for example, mineral oils and/or polyalcohols and/or polyoxyethylene compounds, for example, the mineral oils and surface-active substances mentioned in Netherlands Patent Application No. 7613453. The quantity of the adjuvant to be used may vary between wide limits dependent on the application and usually is between 10 and 10,000 ml per hectare.

The new compounds according to the invention having the general formula I may be prepared by reacting a compound of the general formula

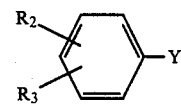

wherein
R₂ and R₃ have the meanings given hereinbefore, and

Y is an amino group or a dichloromethyleneamino group, with a compound of the general formula

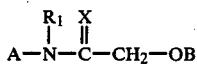

wherein
 $R_1$ and X also have the meanings given hereinbefore, and
 A and B together constitute an N-lower alkyl-iminomethylene group or both represent hydrogen atoms,
with the proviso that
 (a) if Y is an amino group, A and B together constitute an N-lower alkyl-iminomethylene group, and
 (b) if Y is a dichloromethyleneamino group, A and B are both hydrogen atoms.

More particularly, the new compounds according to the invention having the general formula I may be prepared by reacting a compound of the general formula

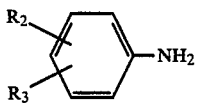

wherein $R_2$ and $R_3$ have the meanings given hereinbefore,
with a compound of the general formula

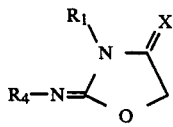

or a salt thereof with an organic or inorganic acid, wherein
 $R_1$ and X have the meanings given hereinbefore, and $R_4$ is a lower alkyl group,
or by reacting a compound of the general formula

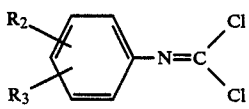

wherein $R_2$ and $R_3$ have the meanings given hereinbefore,
with a compound of the general formula

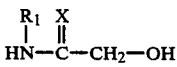

wherein $R_1$ and X have the meanings given hereinbefore.

The last-mentioned reaction, in which a substituted N-dichloromethylene aniline is reacted with an N-substituted glycolic acid amide while splitting off two molecules of HCl, is preferably carried out in an inert organic solvent, such as an aromatic hydrocarbon, for example, toluene, in the presence of an organic base, such as an amine, for example, triethyl amine, at a reaction temperature between room temperature and the boiling-point of the solvent used. The reaction may also be carried out in a two-phase system, in which the first phase is formed by a solution of the reaction components in a suitable polar organic solvent, such as a chlorinated hydrocarbon, for example, methylene chloride or chloroform, and the second phase is an aqueous solution of an inorganic base, for example sodium hydroxide solution or potassium hydroxide solution. This reaction is also preferably carried out at room temperature or a slightly elevated temperature. The substituted N-dichloromethyleneaniline needed for the reaction may be prepared, for example, by chlorinating the corresponding formanilide or isothiocyanate under oxidative reaction conditions, for example, with a mixture of sulphuryl chloride and thionyl chloride. This latter reaction, starting from the formanilide, is preferably carried out at a slightly reduced temperature, for example, in excess thionyl chloride as a solvent; if desired, an inert organic solvent may also be used.

The above-mentioned reaction in which a substituted aniline is reacted with a 2-lower alkylimino oxazolidinone-4 while splitting off a lower alkylamine, is preferably carried out in an inert organic solvent, such as an aromatic hydrocarbon, for example, toluene or xylene, preferably under such conditions that the lower alkylamine is distilled off during the reaction. It is therefore of advantage to use during the reaction an elevated temperature and/or reduced pressure. The 2-lower alkylimino-oxazolidinone-4 needed for the reaction may be prepared by reacting N,N'-bis(lower alkyl) urea with monochloroacetylchloride, preferably in an organic solvent, such as an aromatic hydrocarbon, for example, toluene, at elevated temperature.

As a particular aspect of the invention it was found that the last-mentioned reaction for preparing the final product. i.e. the reaction between a substituted aniline and a 2-lower alkylimino-oxazolidinone-4, rapidly and in a high yield leads to the desired product if the iminooxazolidinone-4 in the form of a salt with a mineral acid, in particular the HCl-salt, is reacted with the substituted aniline. This reaction is carried out in a polar organic solvent, preferably at a temperature between room temperature and the boiling-point of the solvent. As suitable solvents are to be considered lower alcohols, for example, methanol and ethanol, or ethers, for example, dioxane and tetrahydrofurane.

Compounds of the general formula I, wherein $R_2$ is a (halogenated) alkylsulphinyl or alkylsulphonyl group, can also be prepared by oxidizing the corresponding (halogenated) alkylthiocompound, e.g., with hydrogen peroxide or a peroxycarboxylic acid, preferably in a polar organic solvent.

Compounds of the general formula I, wherein $R_2$ is a halogenated or non-halogenated alkoxy or alkylthio group, can also be prepared by reacting the corresponding hydroxy or mercaptocompound with a suitable halogenated or nonhalogenated alkylating agent, preferably in a polar organic solvent and under the influence of a basic substance.

Compounds of the general formula I, wherein X is a sulphur atom can also be prepared by converting the corresponding oxazolidinone-4 with a suitable sulphur containing compound, e.g. phosporus pentasulphide, in an inert organic solvent.

Compounds of the general formula I, wherein $R_2$ is a (halogenated) alkylsulphonyloxy group, can also be prepared by reacting the corresponding hydroxy compound with a suitable sulphonyl halogenide, preferably in the presence of a base.

The invention will hereinafter be described in greater detail with reference to the ensuing specific examples.

EXAMPLE I

Preparation of 2-(3-trifluoromethylphenylimino)-3-methyloxazolidinone-4 (1)

(a) A suspension of 44 g of N,N'-dimethylurea in 250 ml of toluene, to which 62 g of monochloroacetyl chloride has been added, is heated on a steam bath for 6 hours, HCl escaping. After leaving to stand overnight, the formed solid, viz. the HCl salt of 2-methylimino-3-methyloxazolidinone-4, is sucked off, washed successively with toluene and diethyl ether, and dissolved in 500 ml of methanol. After adding excess of triethylamine, the reaction mixture is evaporated, after which the residue is taken up in 500 ml of diethyl ether and is filtered. The filtrate is treated with charcoal and evaporated; the residue is recrystallised from diisopropyl ether and melts, after drying, at 46° C. The yield of 2-methylimino-3-methyloxazolidinone-4 is 46 g. If desired, the substance may be recrystallised from petroleum ether (40–60) and then melts at 48° C., or be distilled in vacuo: boiling-point 100°–101° C./1600 Pa; melting-point 45°–48° C.

(b) A solution of 4.83 g of 3-trifluoromethylaniline and 4.22 g of the 2-methylimino-3-methyloxazolidinone-4, obtained according to example I(a), in 25 ml of toluene is refluxed for approximately 2 days. After evaporating, the residue is taken up in diethyl ether, after which the solution in ether is washed successively with 2N hydrochloric acid (3 times) and with water to neutral. After evaporating the solvent, the residue is recrystallised from petroleum ether (40–60). The desired 2-(3-trifluoromethylphenylimino)-3-methyloxazolidinone-4 is obtained in a yield of 5.70 g; melting point 52.54° C. Xylene may be used instead of toluene as a solvent with the same result. The product may also be purified by distillation; boiling-point 182°–183° C./1600 Pa; melting-point 54°–55° C.

The following compounds are prepared in a corresponding manner; the numbers of the compounds correspond to the numbers used in the specification hereinbefore. In addition 2-(3-hydroxyphenylimino)-3-methyloxazolidinone-4, starting substance for the preparation of compounds nos. (39) and (43) is prepared

| Comp. no. | Phys. characteristics | Comp. no. | Phys. characteristics |
|---|---|---|---|
| (2) | oil; $R_f(CH_2Cl_2)$ 0.45 | (15) | melting-point 109° C. |
| (3) | melting-point 76° C. | (17) | melting-point 115° C. |
| (4) | melting-point 110° C. | (18) | oil; $R_f(CH_2Cl_2)$ 0.45 |
| (6) | oil; $R_f(CH_2Cl_2)$ 0.25 | (19) | oil; $R_f(CH_2Cl_2)$ 0.15 |
| (7) | melting-point 128° C. | (20) | melting-point 88° C. |
| (8) | oil; $R_f(CH_2Cl_2)$ 0.20 | (21) | oil; $R_f(CH_2Cl_2)$ 0.25 |
| (9) | oil; $R_f(CH_2Cl_2)$ 0.18 | (23) | melting-point 139° C. |
| (10) | oil; $R_f(CH_2Cl_2)$ 0.22 | (24) | melting-point 75° C. |
| (11) | melting-point 79° C. | (25) | melting-point 130° C. |
| (12) | melting-point 81° C. | (27) | melting-point 133° C. |
| (13) | melting-point 96° C. | (29) | melting-point 174° C. |
| (14) | melting-point 139° C. | | |

EXAMPLE II 87.5 g of the HCl-salt of 2-methylimino-3-methyloxazolidinone-4 are added to a solution of 80.5 g of 3-trifluoromethylaniline in 200 ml of methanol, after which the reaction mixture is stirred at room temperature until a bright solution has been obtained. The starting 2-methylimino-3-methyloxazolidinone HCl-salt has been obtained as described in example I(a). After leaving to stand overnight at room temperature, the solvent is distilled off under reduced pressure at approximately 25° C. after which the residue is stirred with water, sucked off and washed with water. The desired 2-(3-trifluoromethylphenylimino)-3-methyloxazolidinone-4 is directly obtained in a pure form in a yield of 113 4 g; melting-point 54°–55° C. Dioxane may be used as a solvent to obtain the same result.

In a corresponding manner the following compounds are prepared, as well as 2-(3-mercaptophenylimino)-3-methyloxazolidinone-4, starting substance for the preparation of compounds nos (36), (37), (41) and (42).

| Compound no. | Phys. characteristics |
|---|---|
| (16) | melting point 60.5–62° C. |
| (22) | melting point 79–81° C. |
| (26) | boiling point 146–148° C./0.8 mm |
| (27) | melting point 131–133° C. |
| (28) | $R_f(CH_2Cl_2/CH_3CN = 19/1)$ 0.35 |
| (32) | boiling point 127–128° C./0.2 mm |
| (33) | $R_f(CH_2Cl_2/CH_3CN = 19/1)$ 0.40 |
| (34) | melting point 110.5–111.5° C. |
| (40) | boiling point 138–142° C./0.25 mm |
| (45) | $R_f(CH_2Cl_2/C_2H_5OC_2H_5 = 4/1)$ 0.50 |
| (47) | melting point 63.5–68° C. |

EXAMPLE III

Preparation of 2-(3-trifluoromethylphenylimino)-3-methyloxazolidinone-4 (1)

(a)-51.5 g of 3-trifluoromethylformanilide are added, while stirring, to a mixture of 22 ml (36.4 g) of sulphuryl chloride and 82 ml (134 4 g) of thionyl chloride at a temperature below 10° C. The reaction mixture is then stirred at room temperature for 18 hours, after which the thionylchloride is distilled off under reduced pressure. The residue is distilled in vacuo. The desired N-dichloromethylene-3-trifluoromethylaniline is obtained in a yield of 43.1 g; liquid; boiling-point 109°–117° C./(47–49)$10^2$Pa.

(b) 3 87 g of the N-dichloromethylene-3-trifluoromethylaniline obtained according to example III(a) are added dropwise at room temperature to a suspension of 1.57 g of N-methylglycolic acid amide and 5.0 ml (3.64 g) of triethylamine in 20 ml of dry toluene while stirring. After stirring for approximately 20 hours at room temperature, the precipitate is sucked off and washed with dry diethyl ether. The total organic phase (toluene solution and wash liquid) is then washed successively with dilute sodium hydroxide solution and water and is then dried. After evaporation a syrupy liquid is obtained in a yield of 3.87 g. The desired 2-(3-trifluoromethylphenylimino)-3-methyloxazolidinone-4 can be obtained in a pure form by column chromatography (silica gel as an adsorption agent, methylene chloride as an eluent), or by distillation. The resulting substance is identical to that prepared according to example I and melts at 54°–55° C. In a corresponding manner compound no. (5) is prepared; melting point 50°–53° C.

EXAMPLE IV

Preparation of 2-(3-trifluoromethylsulphinylphenylimino)-3-methyloxazolidinone-4 (30)

To an ice-cooled solution of 43.5 g of 2-(3-trifluoromethylthiophenylimino)-3-methyloxazolidinone-4, obtained according to Example I, in 500 ml of dichloromethane is added portionwise, while stirring 33 g of ca. 85% 3-chloroperbenzoic acid. After stirring at room temperature overnight, 500 ml of a 5% sodium bicarbonate solution are added. The layers are separated and then the organic layer is washed successively two times with 100 ml of sodium bicarbonate solution and with 100 ml of water. After drying and evaporating the solvent the title compound is obtained as a liquid in a yield of 46.3 g. The compound is purified by destillation at 197°–202° C./1.8 mm Elemental analysis: 42.86% C (calc. 43.14), 2.93% H (calc. 2.96), 18.88% F (calc. 18.61), 10.18% S (calc 10.47) and 9.10% N (calc. 9.15). $R_f(CH_2Cl_2/CH_3CN=95/5)$ 0.25.

In a corresponding manner, in which, however, at least two times the above quantity of 3-chloroperbenzoic acid is used, the corresponding sulphonyl compound (31) is prepared. $R_f(CH_2Cl_2/CH_3CN=95/5)$ 0.44. Elemental analysis: 41.13% C (calc. 41.00), 2.91% H (calc. 2.82), 17.24% F (calc. 17.69), 9.91% S (calc. 9.95) and 8.63% N (calc. 8. 69).

In a corresponding manner the following sulphonyl compounds are prepared from their corresponding thio compounds:

compound no. (38): $R_f(CH_2Cl_2/C_2H_5OC_2H_5=3/1)$ 0.50;

compound no. (44): $R_f(CH_2Cl_2)$ 0.30; and compound no. (46): $R_f(CH_2Cl_2/C_2H_5OC_2H_5=3/1)$ 0.50.

EXAMPLE V

Preparation of 2-[3-(1,1,2,2-tetrafluoroethylthio)phenylimino]-3-methyloxazolidinone-4 (36)

At room temperature gazeous 1,1,2,2-tetrafluoroethylene is introduced into a solution of 2.22 g of 2-(3-mercaptophenylimino)-3-methyloxazolidinone-4, obtained according to Example II, and 0.3 ml of triethylamine in 30 ml of acetonitrile. After 0.5 hour the solution is evaporated and the desired compound is obtained as a slightly yellow liquid in a yield of 3.2 g. $R_f(CH_2Cl_2/C_2H_5OC_2H_5=4/1)$ 0.60.

In a corresponding manner compound no. (37) is prepared: $R_f(CH_2Cl_2/C_2H_5OC_2H_5=4/1)$ 0.70.

EXAMPLE VI

Preparation of 2-(3-trifluoromethylphenylimino)-3-methyloxazolidine-4-thione (35)

To a stirred suspension of 5 16 g of 2-(3-trifluoromethylphenylimino)-3-methyloxazolidinone-4, obtained according to Example II, and 4.88 g of phosphorus pentasulphide in 30 ml of bis(2-methoxyethyl)ether is added portionwise 6.72 g of sodium bicarbonate. The clear solution is heated at 60° C. for two hours, then cooled down to room temperature and diluted with water. The formed precipitate is filtered, washed with water and dissolved in diethylether. After drying the organic phase, the solvent is evaporated, yielding the desired product in a quantity of 4.3 g; melting point 84°–86° C.

EXAMPLE VII

Preparation of 2-(3-isopropoxyphenylimino)-3-methyloxazolidinone-4 (39)

A solution of 1 65 g of 2-(3-hydroxyphenylimino)-3-methyloxazolidinone-4, prepared according to Example I, in 25 ml of acetonitrile is refluxed with 4.5 ml of isopropylbromide in the presence of 1.38 g of potassium carbonate for three days. After evaporation of the solvent, addition of water and extraction with dichloromethane, the organic layer is washed with 2N hydrochloric acid and water successively and dried. After evaporating the organic solvent the title compound is obtained as a solid substance, melting at 81.5°–85° C.; yield 1.58 g.

In a corresponding manner, in which, if desired an alkyliodide instead of an alkylbromide may be used, the following compounds are prepared from their corresponding mercaptophenylimino compound:

compound no. (41): $R_f(CH_2Cl_2/C_2H_5OC_2H_5=4/1)$ 0.40; and compound no (42): $R_f(CH_2Cl_2/C_2H_5OC_2H_5=4/1)$ 0.45.

EXAMPLE VIII

Preparation of 2-(3-trifluoromethylsulphonyloxyphenylimino)-3-methyloxazolidinone-4 (43)

To a suspension of 3 1 g of 2-(3-hydroxyphenylimino)-3-methyloxazolidinone-4, obtained according to Example I, in 10 ml of γ-collidine is added 1.8 ml (approx. 3.0 g) of trifluoromethylsulphonylchloride at 0°–5° C. After stirring for 24 hours, the reaction mixure is evaporated, the residue is taken up in 25 ml of dichloromethane, successively washed with 2N hydrochloric acid and water, and dried. After evaporation the desired product is obtained in a yield of 4.6 g; orange oil; $R_f(CH_2Cl_2/CH_3CN=19/1)$ 0.30.

EXAMPLE IX (a) Preparation of a solution of an active substance, viz. 2-(3-trifluoromethylphenylimino)-3-methyloxazolidinone-4 (1) in a water-miscible liquid ("liquid").

10 g of the above active substance are dissolved in a mixture of 10 ml of isophorone and approximately 70 ml of dimethylformamide, after which polyoxyethyleneglycol ricinyl ether is added as an emulsifier in a quantity of 10 g.

In a corresponding manner the other active substances are processed to 10% of 20% "liquids".

In a corresponding manner "liquids" are obtained in N-methylpyrrolidone and isophorone as solvents.

(b) Preparation of a solution of the active substance in an organic solvent.

10 g of the active substance to be investigated are dissolved in 1 000 ml of acetone in the presence of 1.67 g of an emulsifier mixture consisting of an alkylarylsulphonate mixture and nonylphenolpolyoxyethylene. This solution, after dilution to be desired concentration, is used as a spray liquid.

(c) Preparation of an emulsifiable concentrate of the active substance.

10 g of the active substance to be investigated are dissolved in a mixture of 15 ml of isophorone and 70 ml of xylene; 5 g of a mixture of a polyoxyethylene sorbitan ester and an alkylbenzene sulphonate as an emulsifier are added to this solution.

(d) Preparation of a dispersible powder (W.P.) of the active substance.

25 g of the active substance to be investigated are mixed with 68 g of kaolin in the presence of 2 g of sodium butylnaphthalene sulphonate and 5 g of lignine sulphonate.

(e) Preparation of a suspension concentrate (flowable) of the active substance.

A mixture of 10 g of active substance, 2 g of lignine sulphonate and 0.8 g of a sodium alkyl sulphate is replenished with water to a total quantity of 100 ml.

(f) Preparation of a granule of the active substance.

7.5 g of active substance, 5 g of sulphite lye and 87.5 g of ground dolomite are mixed, after which the resulting mixture is processed to a granular composition by means of the so-called compacting method.

EXAMPLE X

Control of Weeds (Pre-Emergence) in the Glasshouse

Compounds according to the invention are used in a quantity of 3 kg per hectare against the following weeds: *Galinsoga parviflora* (small-flowered g, Gp), *Chenopodium album* (common lambsquarters, Ca), *Polygonum convolyulus* (wild buckwheat, Pc) and *Panicum miliaceum* (millet Pm). Before emergence of the weeds the sowed soil is sprayed with a spray liquid obtained according to example IX(b) by means of a spraying device suitable for this purpose. The herbicidal activity is evaluated after 3 weeks. The damage of the weed plants in percentage is recorded in table A below. For comparison, the known substance 2-(4-chlorophenylimino)-3-methyloxazolidine has also been tested.

TABLE A

| compound no. | percentage damage to | | | |
|---|---|---|---|---|
| | Pm | Ca | Gp | Pc |
| (1) | 90–100 | 90–100 | 90–100 | 90–100 |
| (3) | 90–100 | 90–100 | 90–100 | 90–100 |
| (5) | 90–100 | 90–100 | 90–100 | 90–100 |
| (7) | 90–100 | 90–100 | 90–100 | 90–100 |
| (10) | 90–100 | 90–100 | 90–100 | 90–100 |
| (11) | 90–100 | 90–100 | ca. 30 | 90–100 |
| (12) | 90–100 | 90–100 | 90–100 | 90–100 |
| (13) | 90–100 | 90–100 | 90–100 | ca. 70 |
| (14) | 90–100 | 90–100 | 90–100 | 90–100 |
| (15) | 90–100 | 90–100 | 90–100 | 90–100 |
| (16) | 90–100 | 90–100 | 90–100 | 90–100 |
| (17) | ca. 70 | 90–100 | 90–100 | 90–100 |
| (18) | 90–100 | 90–100 | 90–100 | 90–100 |
| (19) | 90–100 | 90–100 | ca. 70 | 90–100 |
| (20) | 90–100 | 90–100 | 90–100 | 90–100 |
| (22) | 90–100 | 90–100 | 90–100 | 90–100 |
| (23) | 90–100 | 90–100 | 90–100 | 90–100 |
| (24) | 90–100 | ca. 70 | ca. 70 | ca. 70 |
| (25) | 90–100 | 90–100 | 90–100 | ca. 70 |
| (26) | 90–100 | 90–100 | 90–100 | 90–100 |
| (27) | 90–100 | 90–100 | 90–100 | 90–100 |
| (28) | 90–100 | 90–100 | 90–100 | 90–100 |
| (29) | 90–100 | 90–100 | 90–100 | 90–100 |
| (32) | 90–100 | 90–100 | 90–100 | 90–100 |
| (33) | ca. 30 | 90–100 | 90–100 | 90–100 |
| (34) | 90–100 | 90–100 | 90–100 | 90–100 |
| (35) | 90–100 | 90–100 | 90–100 | 90–100 |
| (36) | 90–100 | 90–100 | 90–100 | 90–100 |
| (37) | 90–100 | 90–100 | 90–100 | 90–100 |
| (38) | 90–100 | 90–100 | 90–100 | 90–100 |
| (39) | 90–100 | 90–100 | | 90–100 |
| (40) | 90–100 | 90–100 | 90–100 | 90–100 |
| known | 0–10 | 0–10 | 0–10 | 0–10 |

EXAMPLE XI

Control of Weeds (p.s.i.) in the Glasshouse

Compounds according to the invention in the same formulation as indicated in example X are mixed through the top layer of the soil in a quantity of 3 kg per hectare. Then the following weeds are sowed: *Echinochloa crusgalli* (barnyard grass, Ec), *Polygonum aviculare* (knotgrass, Pa), *Ipomoea purpourea* (common morning glory's, Ip) and *Senecio vulgaris* (common groundsel, Sv). After 3 weeks the herbicidal activity is evaluated. The damage to the weed plants in % is recorded in Table B below.

TABLE B

| compound no. | percentage damage to | | | |
|---|---|---|---|---|
| | Ec | Pa | Ip | Sv |
| (1) | 90–100 | 90–100 | 90–100 | 90–100 |
| (3) | 90–100 | 90–100 | 90–100 | 90–100 |
| (7) | 90–100 | 90–100 | 90–100 | 90–100 |
| (12) | ca. 70 | ca. 70 | ca. 70 | 90–100 |
| (14) | 90–100 | ca. 70 | 90–100 | 90–100 |
| (20) | 90–100 | 90–100 | 90–100 | 90–100 |
| (23) | 90–100 | 90–100 | ca. 70 | ca. 70 |

EXAMPLE XII

Control of Weeds (Pre-Emergence) in the Glasshouse

In the same manner as described in example X compounds according to the invention are tested on *Panicum miliaceum* (millet, Pm), *Chenopodium album* (common lambsquarters, Ca) and *Polygonum convolyulus* (wild buckwheat, Pc), this time, however, in different concentrations. The results are recorded in Table C.

TABLE C

| compound no | dosage (g/ha.) | percentage damage to | | |
|---|---|---|---|---|
| | | Pm | Ca | Pc |
| (1) | 3000 | 90–100 | 90–100 | 90–100 |
| | 1000 | 90–100 | 90–100 | 90–100 |
| | 300 | 90–100 | 90–100 | 90–100 |
| (3) | 3000 | 90–100 | 90–100 | 90–100 |
| | 1000 | 90–100 | 90–100 | 90–100 |
| | 300 | ca. 30 | ca. 30 | ca. 30 |
| (10) | 3000 | 90–100 | 90–100 | 90–100 |
| | 1000 | 90–100 | 90–100 | 90–100 |
| | 300 | 90–100 | 90–100 | 90–100 |
| (15) | 3000 | 90–100 | 90–100 | 90–100 |
| | 1000 | 90–100 | 90–100 | 90–100 |
| | 300 | ca. 70 | 90–100 | ca. 30 |
| (18) | 3000 | 90–100 | 90–100 | 90–100 |
| | 1000 | 90–100 | 90–100 | 90–100 |
| | 300 | 90–100 | 90–100 | ca. 70 |
| (20) | 3000 | 90–100 | 90–100 | 90–100 |
| | 1000 | 90–100 | 90–100 | 90–100 |
| | 300 | ca. 70 | 90–100 | ca. 30 |
| (23) | 3000 | 90–100 | 90–100 | 90–100 |
| | 1000 | 90–100 | 90–100 | ca. 70 |
| | 300 | ca. 70 | ca. 30 | ca. 70 |
| (29) | 3000 | 90–100 | 90–100 | 90–100 |
| | 1000 | 90–100 | 90–100 | 90–100 |
| | 300 | ca. 30 | 0–10 | ca. 30 |
| (32) | 3000 | 90–100 | 90–100 | 90–100 |
| | 1000 | 90–100 | 90–100 | 90–100 |
| | 300 | ca. 70 | 90–100 | 90–100 |
| (36) | 3000 | 90–100 | 90–100 | 90–100 |
| | 1000 | 90–100 | 90–100 | 90–100 |
| | 300 | 90–100 | 90–100 | 90–100 |
| (40) | 3000 | 90–100 | 90–100 | 90–100 |
| | 1000 | 90–100 | 90–100 | 90–100 |
| | 300 | 90–100 | 90–100 | 90–100 |

EXAMPLE XIII

Selective Control of Various Weeds (Pre-Emergence)

Compounds according to the invention are tested in the glasshouse in a formulation according to example IX(b) in various concentrations on various weeds, namely *Panicum miliaceum* (millet), *Chenopodium album* (common lambsquarters) and *Polygonum convolvulus* (wild buckwheat). Moreover the following crops are present: *Gossilum hirsutum* (cotton, Gh) and *Glycine max* (soya, Gm). The tests are carried out in the same manner as in example V. After 3 weeks the damage to the plants is evaluated, the average damage to the weeds being determined. The damage is recorded in percent in Table D below.

TABLE D

| compound | | percentage damage to | | |
|---|---|---|---|---|
| no. | dosage (g/ha.) | weeds | Gh | Gm |
| (1) | 300 | 90–100 | 0–10 | ca. 30 |
| (3) | 1000 | 90–100 | ca. 30 | 0–10 |
| (5) | 3000 | 90–100 | 0–10 | ca. 30 |
| (10) | 300 | 90–100 | 0–10 | ca. 30 |
| (12) | 3000 | 90–100 | 0–10 | ca. 30 |
| (13) | 3000 | 80–90 | 0–10 | ca. 30 |
| (15) | 1000 | 90–100 | 0–10 | 0–10 |
| (16) | 1000 | 90–100 | 0–10 | ca. 30 |
| (18) | 300 | 80–90 | 0–10 | 0–10 |
| (19) | 3000 | 90–100 | 0–10 | 0–10 |
| (20) | 1000 | 90–100 | 0–10 | ca. 30 |
| (22) | 1000 | 75–80 | 0–10 | 0–10 |
| (23) | 1000 | 80–90 | 0–10 | ca. 30 |
| (24) | 3000 | 75–80 | 0–10 | ca. 30 |
| (25) | 3000 | 80–90 | 0–10 | ca. 30 |
| (27) | 3000 | 90–100 | 0–10 | 0–10 |
| (28) | 1000 | 90–100 | 0–10 | ca. 30 |
| (29) | 1000 | 90–100 | ca. 30 | ca. 30 |
| (34) | 3000 | 90–100 | 0–10 | 0–10 |
| (37) | 3000 | 90–100 | 0–10 | 0–10 |
| (38) | 1000 | 80–90 | 0–10 | ca. 30 |
| (40) | 300 | 90–100 | 0–10 | ca. 30 |

We claim:

1. A substituted 2-phenyliminooxazolidine compound of the formula

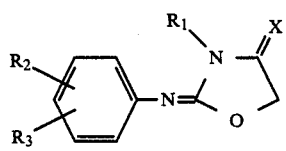

wherein $R_1$ is an unsubstituted alkyl group having 1–6 carbon atoms or an alkyl group which has 1–6 carbon atoms and which is substituted by halogen or hydroxy, or an alkenyl or alkynyl group having 2–6 carbon atoms;

$R_2$ is a halogen atom; a nitro group; a cyano group; a benzyl, phenyl, phenoxy, phenylthio, phenylsulphinyl, phenylsulphonyl or phenylsulphonyloxy group, which groups are unsubstituted or substituted with a substituent selected from the group consisting of halogen, lower alkyl, lower alkoxy, lower haloalkyl, lower haloalkoxy, nitro, cyano and lower alkoxycarbonyl; or a halogenated or non-halogenated alkyl, alkoxy, alkylthio, alkylsulphinyl, alkylsulphonyl or alkylsulphonyloxy group having 1–4 carbon atoms;

$R_3$ is a hudrogen atom, a halogen atom, or an alkyl group having 1–4 carbon atoms; and X is O or S;

or a herbicidally acceptable salt of this compound with an organic or inorganic acid.

2. A compound as claimed in claim 1 of the formula

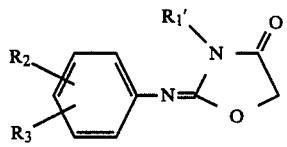

wherein $R_2$ is a substituent having the meaning given in claim 1 and which is attached to the benzene ring in the meta position with respect to the imino-N, $R_3$ also has the meaning given in claim 1, and $R_1'$ is an alkyl group having 1–4 carbon atoms, or a herbicidally acceptable salt of this compound with an organic or inorganic acid.

3. A compound as claimed in claim 1 of the formula

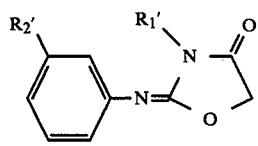

wherein $R_1'$ has the meaning given in claim 2, and $R_2'$ is a halogenated alkyl, alkoxy, alkylsulphinyl, alkylsulphonyl or alkylthio group having 1–4 carbon atoms, or a herbicidally acceptable salt of this compound with an organic or inorganic acid.

4. A herbicidal and/or algicidal composition which, in addition to a solid or liquid inert carrier material, comprises a substituted 2-phenylimino-oxazolidine compound as the active substance, characterized in that the active substance is a compound of the formula I, wherein $R_1$, $R_2$, $R_3$ and X have the meanings given in claim 1, or a salt of this compound with an organic or inorganic acid, said salt being acceptable for herbicidal application.

5. A composition as claimed in claim 4, characterized in that the active substance is a compound of the formula II, wherein $R_2$ and $R_3$ have the meanings given in claim 1 and $R_1'$ has the meaning given in claim 2, or a salt of this compound with an organic or inorganic acid, said salt being acceptable for herbicidal application.

6. A composition as claimed in claim 4, characterized in that the active substance is a compound of the formula III, wherein $R_1'$ has the meaning given in claim 2 and $R_2'$ has the meaning given in claim 3, or a salt of this compound with an organic or inorganic acid, said salt being acceptable for herbicidal application.

7. A method of controlling and/or preventing undesired plant growth, characterized in that the said plants or their plots are treated with a composition as claimed in any of the claims 4–6 in a dosage from 0.01 to 10 kg of active substance per hectare, preferably from 0.1 to 3 kg per hectare.

* * * * *